(12) United States Patent
Soukup

(10) Patent No.: US 8,466,297 B2
(45) Date of Patent: Jun. 18, 2013

(54) MANUFACTURING PROCESS FOR (S)-PREGABALIN

(76) Inventor: Milan Soukup, Sarasota, FL (US)

( * ) Notice: Subject to any disclaimer, the term of this patent is extended or adjusted under 35 U.S.C. 154(b) by 57 days.

(21) Appl. No.: 12/925,782

(22) Filed: Nov. 1, 2010

(65) Prior Publication Data

US 2012/0123134 A1 May 17, 2012

(51) Int. Cl.
C07D 207/26 (2006.01)

(52) U.S. Cl.
USPC .......................................... 548/551; 548/552

(58) Field of Classification Search
USPC .................................. 548/551, 552
See application file for complete search history.

(56) References Cited

U.S. PATENT DOCUMENTS

| | | | |
|---|---|---|---|
| 5,563,175 A | 10/1996 | Silverman |
| 6,001,876 A | 12/1999 | Singh |
| 6,197,819 B1 | 3/2001 | Silverman |
| 2004/0116507 A1 | 6/2004 | Differding et al. |
| 2010/0197939 A1 | 8/2010 | Ortuno et al. |

FOREIGN PATENT DOCUMENTS

IN 2010/CHE/2339 * 9/2010

OTHER PUBLICATIONS

Greene, T. W., Wuts, P. G. M., "Protective Groups in Organic Synthesis," 3rd ed., John Wiley & Sons: New York, 1991.*

* cited by examiner

*Primary Examiner* — Robert Havlin

(57) ABSTRACT

The present invention relates to a novel manufacturing process and novel intermediates useful in the synthesis of pharmaceutically active compounds of general formula I used for treatment of epilepsy, neuropathic pain, anxiety and social phobia. The invention describes preparation of enantiomerically pure (S)-Pregabalin from chiral pyrrolidin-2-one of formula IV.

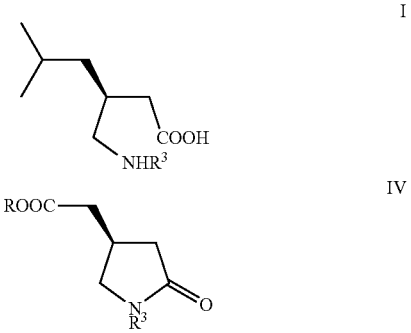

5 Claims, No Drawings

MANUFACTURING PROCESS FOR (S)-PREGABALIN

BACKGROUND OF THE INVENTION

4-Amino acids of a general formula I, having the 3S-configuration,

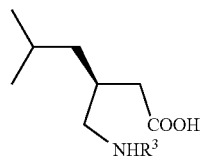

I especially compound such as (S)-Pregabalin, wherein $R^3$ represents hydrogen, are used for treatment of epilepsy, neuropathic pain, anxiety and social phobia. The pharmacological activity of Pregabalin is primarily attributable to the (S)-enantiomer and thus, several methods have been developed to prepare enantiomerically pure (S)-Pregabalin.

After discovery of the biological activity of (S)-Pregabalin first synthesis has been disclosed in U.S. Pat. No. 5,563,175 and EP 641330. However, the disclosed process is lengthy (more than 10 steps), has a low overall yield and uses pyrophoric or expensive reagents, such as n-butyl lithium or a chiral auxiliary as (+)-4-methyl-5-phenyl-2-oxazolidinone, which definitely limits use on an industrial scale.

In Org. Proc. Res. & Develop. 1997, 1, 26 several other routes to (S)-Pregabalin are reported. Two processes of particular economical interest are disclosed in EPA828704 and EPA830338. In the first patent, 3-isobutyl glutaric acid, prepared from isovaleraldehyde and ethyl cyanoacetate, serves as a key intermediate, which is transformed via the corresponding cyclic anhydride to an amine which can be resolved in a classical manner with chiral phenyl ethylamine. The amide function is then subjected to a Hoffmann degradation leading to (S)-Pregabalin. Improved variations of this process have been disclosed in WO2006/122255, WO2006/122258, WO2006/122259, WO2006/136087, WO2007/035789, WO2007/035790 and WO2007/139933.

In EPA830338 from isovaleraldehyde and diethyl malonate racemic Pregabalin was prepared in five steps and the racemate then resolved. The resolution of the racemate at the end of the synthesis makes the process very costly and inefficient because the (R)-isomer cannot be recycled and has to be discarded. A variation of this process with resolution, prior the reduction of the cyano group, was also disclosed in WO2007/143152. Both processes suffer from disadvantage as lengthy synthesis and low overall yield.

An asymmetric synthesis of an intermediate on the route to (S)-Pregabalin incorporates a homogeneous hydrogenation with chiral phosphine-based ligands (WO2001/55090 and WO2005/087370). The starting material is prepared in 3 steps using carbon monoxide which is hazardous and the phosphine ligands which are very expensive.

In WO2006/110783 conversion of chiral 2-(3-methyl-1-nitro-butyl)-malonic acid dialkyl ester to (S)-Pregabalin using reduction/decarboxylation steps was described. All these processes make use of chiral auxiliaries, catalysts or additives which are often difficult to remove from final product.

Enzymatic kinetic resolution of two nitrile-containing Pregabalin precursors has been claimed in WO2005/100580 and WO2006/00904. In WO2007/143113 also an enzymatic resolution via hydrolysis or esterification of racemic substrates have been reported.

In Synthesis 1989, 953 a synthesis of rac.-Pregabalin, starting from (E)-5-methyl-hex-2-enoic acid ethyl ester, which was converted with nitromethane into 5-methyl-3-nitromethyl-hexanoic acid ethyl ester, has been reported. Subsequent catalytic hydrogenation followed by saponification leads to rac.-Pregabalin. Recently an enzymatic hydrolysis of this racemic nitro ester was carried out (Tetrahedron Asymmetry 2008, 19, 945). With enzyme Novozyme 435 enantiomerically enriched (S)-5-methyl-3-nitromethyl-hexanoic acid could be obtained in a good selectivity if the conversion was stopped at 30%.

In US2010/0197939 a long synthesis of (S)-Pregabalin from D-mannitol has been reported which barely can be used for an industrial production.

The best approaches to (S)-Pregabalin use either prochiral 3-isobutyl glutaric anhydride, which is subjected to a desymmetrization step using either a chiral substrate or an enzyme (WO2007/139933), or a prochiral 3-isobutyl glutaric acid or diester thereof, which have been enzymatically desymmetrised (WO2009/158343).

Although many processes for (S)-Pregabalin are reported, still significant improvements in terms of reducing the number of steps and increasing the overall yields are highly desirable to have an efficient and cost effective manufacturing process.

Of particular interest are specifically enzymatic methods on prochiral substrates: Since the undesired (R)-enantiomer cannot be recycled (racemised) and has to be discarded, enzymatic esterification or hydrolysis of prochiral substrates would allow a complete conversion of the substrate providing exclusively (S)-configurated precursor of (S)-Pregabalin in high yield (90-100%).

SUMMARY OF THE INVENTION

The present invention discloses a novel efficient process for the manufacture of enantiomerically pure compounds of general formula I, specifically of (S)-Pregabalin, as shown in Scheme 1:

Schema 1

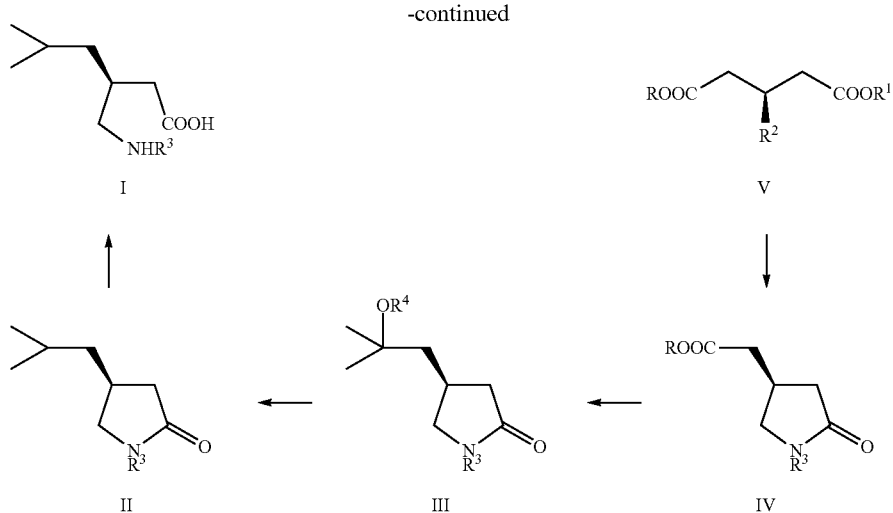

It has been unexpectedly found that the compound of formula I, and a precursor thereof (formula II), can be efficiently prepared in two simple steps from a chiral compound of formula IV which is readily available by an enzymatic desymmetrization of a prochiral substrate of formula VI in almost quantitative yield followed by reductive/cyclization step.

DETAILED DESCRIPTION OF THE INVENTION

The present invention claims a process (Scheme 1) for the preparation of a compound of general formula II, having the (S)-configuration as given in formula,

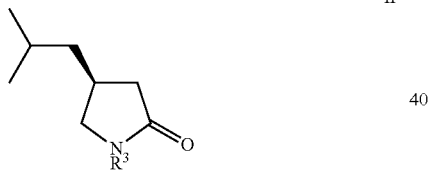

wherein
R³ represents hydrogen, alkyl, aryl, alkylaryl, arylalkyl, trialkylsilyl, with heteroatom(s) substituted alkyl, aryl, alkylaryl, arylalkyl, preferably hydrogen, benzyl, mono-, di- or tri-methoxybenzyl, or other N-protective group, in particular one which together with N forms an amide or carbamate as —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl, —C(O)Obenzyl (Cbz) or —C(O)Otert.-butyl (BOC);
comprising following steps:
a) reaction of the compound of formula IV

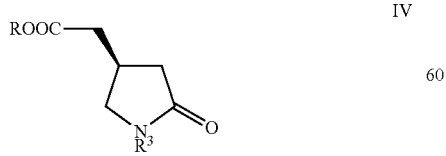

wherein R represents hydrogen, linear or brunched C₁₋₆-alkyl, aryl, alkylaryl, arylalkyl, trialkylsilyl or alkylarylsilyl, preferably hydrogen, -Me, -Et or benzyl, with a reagent containing C₁-fragment such as methyl organometallic reagent, preferably Me-alkali metal or Me-earth alkali metal as Me-Li or MeMghalide, MeMgCl or MeMgBr, followed by alternative protection/activation of tert.-hydroxy group according to as defined for R⁴, providing a compound of formula III,

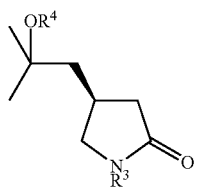

wherein R³ is the same as defined for compound of formula II and
R⁴ represents counter cation as alkali or earth alkali metal cation, preferably Li⁺ or MgCl/Br⁺, or hydrogen, alkyl, alkylaryl, arylalkyl, trialkylsilyl, with heteroatom(s) substituted alkyl, arylalkyl, preferably benzyl, mono-, di- or tri-methoxybenzyl, or other O-protective group, in particular one which together with O forms an ester or carbonate as —C(O)alkyl, —C(O)aryl, —C(O)alkylaryl, —C(O)arylalkyl, —C(O)Oalkyl, —C(O)Oaryl, —C(O)Oalkylaryl, —C(O)Oarylalkyl, preferably acetyl, trifluoroacetyl, formyl, —C(O)OMe, —C(O)OEt, —C(O)Obenzyl (Cbz), or —SO₂Cl or alkyl- or arylsulfonyl, preferably Mesyl, Tosyl, Nosyl or trifluoromethanesulfonyl, or thiocarbonyl derivative as —C(S)Oalkyl or —C(S)Oaryl or —C(S)imidazolyl;
b) reductive removal of —OR⁴ group
  i. either directly via reductive displacement of —OR⁴ group with hydrogen, preferably by homogeneous or heterogeneous hydrogenation in the presence of transition metals as Ra—Ni, Pt, Pd, Ru and Rh, or with other reducing agent as metal hydride via S$_{n2}$ substitution of —OR⁴ group with a hydride, or by a radical-based de-oxygenation, preferably with metal hydride or silanes as Et₃SiH, Cl₃SiH, tris(trimethylsilyl)-silane or Bu₃SnH also in the presence of NaBH₄, or dialkyl phosphites or hypophosphorous acid, ii. or, after thermal, acid or based catalyzed elimination of H—OR⁴, reduction or hydrogenation of the double bond in the compound of formula IIIa, wherein R³ is the same as defined for compound of formula IV.

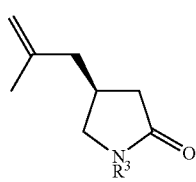

IIIa

When referring to compounds described in the present invention, it is understood that references are also being made to salts thereof.

Depending on the choice of starting materials the compounds of formula II, III, IV and V can be present in the form as enantiomerically pure compounds either as (R)- or (S)-configurated stereo isomers or as the racemates.

In this invention racemic compounds of formulas III, IV and V can be subjected at any stage of the synthesis to a resolution or separation step using (chiral) agent or including an enzymatic step or another separation method known as e.g. preparative HPLC or SMB etc. As the resolution agent any chiral acid or base as commonly used for resolution of nitrogen- or alcohol- or carboxylate-containing compounds, can be used.

In this invention a characteristic of protective groups (R, R¹, R³ and R⁴) is that they can be removed readily (without the occurrence of undesired secondary reactions) for example by solvolysis, reduction, or alternatively under physiological conditions (as e.g. enzymatic cleavage or formation). Different protective groups can be selected so that they can be removed selectively at different stages of the synthesis while other protective groups remain intact. The corresponding alternatives can be selected readily by a person skilled in the art from those given in the standard reference works mentioned in literature (as e.g. Mc Omie "Protective Groups in Organic Chemistry" or Green et al. "Protective Groups in Organic Synthesis") or in the description or in the claims or the Examples.

In the preferred embodiment of the invention the compound of formula IV can be reacted with reagent containing a $CH_3$-nucleophilic building block, which adds twice to the ROOC— group in the compound of formula IV introducing two carbon atoms, preferably two methyl groups. Two or more equivalents of methyl alkali metal or methyl earth alkali metal halide, preferably MeLi or MeMgCl or MeMgBr, dependent on R and R³-groups, have to be used in inert organic solvent such as THF, glyme, diglyme, ethers, preferably THF or diethyl ether, at temperature between −78° C. until reflux, preferably −10° C. to rt. The addition product formed in situ, the tert.-alkoholate of formula III, wherein R⁴ is counter cation as alkali or earth alkali metal cation, preferably Li⁺ or MgCl/Br⁺, can be either directly reacted with an appropriate reagent containing R⁴ group to obtain compound of formula III according to R⁴ definition. Alternatively, the tert.-alkoholate can also be protonated during an aqueous workup and the crude compound of formula III, wherein R⁴ is hydrogen, then converted in an additional step into compound of formula III, dependent again on R⁴ definition.

Preferably the in situ formed Li- or magnesium-alkoholate of formula III is directly reacted with methyl chloroformate, acetanhydride, Mesylchloride, Triflic anhydride, trifluoraceticacid anhydride or even thionylchloride at temperature between −30° C. to rt providing either the activated compound of formula III or an elimination intermediate of formula IIIa.

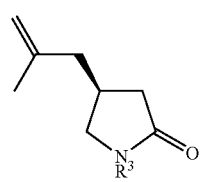

IIIa

Compounds of formula III or IIIa are then subjected to either reduction or hydrogenation, in one or several steps, by a suitable method known to a person skilled in the art for either reductive removal of tert. —OR⁴ group or for reduction of double bond into a single one.

A suitable hydride containing reducing agent, which properly selected does not attack the lactam functional group, can be used. Preferably, the reduction is carried out by selective homogeneous or heterogeneous hydrogenation in the presence of transition metals, preferably Ra—Ni, Pt, Pd or Rh in alcohol as e.g. ethanol, at normal or slightly elevated pressure at rt or temperature above rt.

Examples of possible hydrogenation are in the presence of a suitable transition metal catalysts such as Pt, Pd, Rh, Ru, Ni and Ra—Ni, optionally solid or on a support such as carbon, silica, calcium carbonate etc. Also catalytic transfer hydrogenation using a hydrogen donor from formic acid or salt thereof, hydrazine, cyclohexadiene or silanes in the presence of a transition metal catalyst as defined above, or sulfides such as NaSH etc., or polysulfides, can be used.

As a further embodiment of the invention the protective/activating group —OR⁴ can also be electron withdrawing group according to literature (F. J. McQuillin et al. J. Chem Soc. 1967, 136 or Houben Weyl Vol. 4/1c, pp 73, 379-383.) which can be reductively removed by a suitable method known to a person skilled in the art.

Thiocarbonyl derivatives can also be used which allows radical-based de-oxygenation of the —OR⁴ group. Preferred examples are thiocarbamates, such as imidazolyl derivatives, thiocarbonyls, such as xanthates or thionocyrbonates. Particularly preferred is a N-imidazolyl thionocarbamate. For conversion of the tert.-alkohol into thioncarbonyl derivatives, methods known in the art may be employed. In particular Barton methods as they are described in J. Chem Soc. Perkin Trans 11975, 1574 or in Tetrahedron Letters 1990, 31, 3991 or in J. Amer. Chem Soc. 1981, 103, 933 and ibid. 1983, 105, 4059 can be used. The radical de-oxygenation is performed using standard methodology with reducing agents as e.g. Bu3SnH or tris(trimethylsilyl)silane (Synlett 1990, 705) or NaBH₄. Other silanes can be used as reported in Tetrahedron 1991, 47, 8969 or Tetrahedon 1993, 49, 7193 or Heterocycles 1996, 42, 499 or Tetrahedron Letters 1996, 37, 5877.

As a preferred embodiment of the invention the starting compound of formula IV can be prepared from prochiral compound of formula VI, wherein R₂ is —CH₂NO₂, which is subjected to enzymatic hydrolysis with pig liver esterase (PLAP or PLE), to obtain the S-configurated, or with Porcine pancreatic lipase (PPL), to obtain the R-configurated compound of formula V. After reduction of R² group with e.g. hydrogen in the presence of Ra—Ni the R- or S-compound of formula IV has been obtained in over 90% yield and 99% ee as reported in Tetrahydron Asymmetry 2004, 15, 3323 for compound of formula V, wherein $R^2$ is —$CH_2NO_2$.

Accordingly the prochiral compound of formula VI, wherein $R^2$ is —CN, can also be converted in high yield into R- or S-compound of formula IV as disclosed below:

As a preferred embodiment of the invention the chiral compound of formula V can be prepared i. either enzymatic hydrolysis of compound of formula VI, wherein $R^2$ is —CN and $R^1$ is lower alkyl, preferably methyl, ethyl, propyl or butyl,

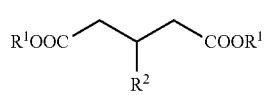

VI ii. or enzymatic esterification of compound of formula VI, wherein $R^2$ is —CN and $R^1$ is hydrogen, with a suitable enzyme which is capable of stereo selective esterification or hydrolysis, The enzymatic hydrolysis of the diester of formula VI is usually carried out by a technique known to a person skilled in the art in water by adding of an appropriate base, preferably aqueous sodium hydroxide, keeping the pH at constant level. The reaction may contain a single or multiple phases and e.g. be a two or three-pase system. Examples of such two- or three-phase systems are described in WO2006/000904 on page 30, lines 14-33. In the preferred embodiment of the invention the reaction is carried out in a aqueous solvent such as water, or a mixture of water and an organic solvent such as methanol, ethanol, THF, which is miscible therewith.

The enzymatic esterification of diacid of formula VI is performed in non aqueous media, in which alkoxy donor are selected from the group consisting of methanol, ethanol propanol, benzyl alcohol, butanol, vinyl acetate, methyl or ethyl acetate.

The conditions used are dependent on selected enzyme. Since prochiral substrates are used, the conversion can be greater than 90% providing chiral compound of formula V with ee-value higher that 95%, dependent on enzyme.

As suitable enzymes several Esterases, Lipases or Proteases can been used: as e.g. pig liver esterase (PLG or PLAP), porcine pancreatic lipase (PPL), a-chemotripsin, Lipase A, B or C from *Candida antartica*, Esterase EstB and EstC from *Burkholderia gladioli*, Esterase BS2 from *Bacillus* species, Esterase BS3 from *Bacillus* Species, *Candida rugosa, Aspergillus niger*, Protease as Subtilisin Carlsberg, Lipase L-5, Lipase from *Aspergillus Oryzae*, Lipase from *Thermomyces lanuginosus*, Lipase from *Thermomyces lanuginosus* mutant, Lipase mutant broad range from *Thermomyces lanuginosus* mutant, Lipase PS amino from *Pseudomonas stutzeri*, Lipase RS from *Rhizopus* spp., Lipase PF from *Pseudomonas fluorescens*, Lipase PC from *Penicillium camenbertii*, Lipase P1 from *Pseudomonas cepacia*, Lipase P2 from *Pseudomonas cepacia*, Lipase AN from *Aspergillus niger*, Lipase A from *Candida Antartica*, Lipase CA(A) from *candida*, Lipase CAL A from *candita*, Lipase AS1 from *Alcaligenes* spp., Lipase AS2 *Alcaligenes* spp., Lipase C2 from *Candida cylindracea*, Lipase C1 from *Candida cylindacea*, Lipase B from *Candida Antartica*, Lipase CA(B) from *Candida antartica*, Lipase CAL B from *Candida antartica*, Lipase CAL B IM, Lipase from *rhinomucor miehei*, Lipase acceptin bulky substrate from fungal mutat, Lipase broad range from fungal, Lipase broad range from fungal muatat, Lipase *mucor* sol from *Mucore miehei*, Lipase *mucor* CF from *Mucore miehei* and Lipase MM from *Mucore Miehei*, Protease alkaline from *Bacillus clausii* or from *Bacillus hludurans*, or *Bacillus licheninformis* or from *Bacillus Fusarium oxysporum* or from *Rhizomucor miehei*.

The enzymes can be used in the form of a crude lysate or in a purified form. Alternatively, the enzymes may be in the form of whole microbiological cells, permeabilized microbial cells, extracts of microbial cells, partially purified enzymes, purified enzymes etc. Preferably, the enzyme is used in the form of crude lysate or lyophilisate.

The enzymes can be immobilized and used as such. Immobilization techniques are known to a person skilled in the art. Useful solid supports include e.g. polymer matrix such as calcium alginate etc.

As further embodiment of the invention the nitrile group in R- or S-configurated compound of formula V can be reductively converted into amino group, either in one or several steps, with an appropriate hydride containing reducing agent, which properly selected, does not attack ester functional group, or as proffered the reduction is carried out by selective homogeneous or heterogeneous hydrogenation as known to a person skilled in the art, preferably with Ra—Ni in alcohol as e.g. ethanol, at normal or slightly elevated pressure at rt or temperature above rt.

Under major conditions the amino group reacts then spontaneously with the present ester function providing the chiral lactam of formula IV, wherein R is preferably hydrogen or a alkali or earth alkali metal salt. For complete cyclization to the lactam of formula IV elevated temperature is often required.

Examples of possible hydrogenation are in the presence of a suitable transition metal catalyst such as Pt, Pd, Rh, Ru, Ni and Ra—Ni, optionally solid or on a support such as carbon, silica, calcium carbonate etc. Also catalytic transfer hydrogenation using a hydrogen donor from formic acid or salt thereof, hydrazine, cyclohexadiene or silanes in the presence of a transition metal catalyst as defined above, or sulfides such as NaSH etc., or polysulfides can be used.

When referring to compounds described in the present invention, it is understood that references are also being made to salts thereof.

For the purpose of this disclosure, a compound is considered to be "enantiomerically pure" if the content of one isomer is higher than 95%, preferably 99%.

The example are provided to illustrate particular aspects of the disclosure and do not limit the scope of the present invention as defined by the claims.

EXAMPLES

Determination of optical purity was carried out with HPLC using chiral columns as Chiralcel OJ-H, Chiralpak AS-H or Chiralpak AD-H from Daicel Chem. Ind. In some cases the optical purity was also determined with NMR-Spectroscopy using chiral Eu-shift reagent. If not mentioned otherwise, all evaporation are performed under reduced pressure, preferably between 5-50 Torr in some case even under high vacuum. The structure of final products, intermediates and starting materials is confirmed by standard analytical methods, e.g.

spectroscopic characteristics as MS or NMR or IR. Abbreviation used are those conventional in the art.

Preparation of (S)-4-(isobutyl)-pyrrolidin-2-on (IIb) from compound (IVb)

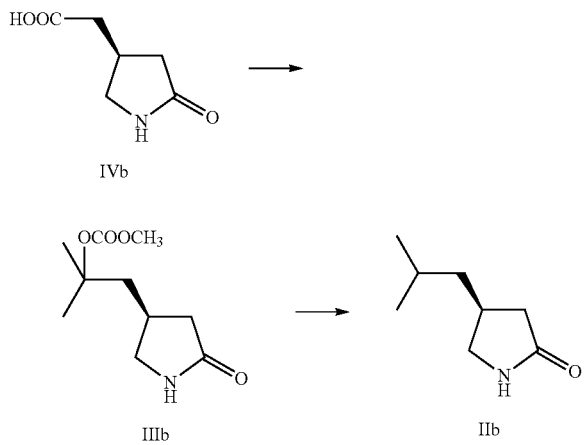

The (S)-4-isobutyl-pyrrolidin-2-one was then hydrolyzed either with 4N—HCl to (S)-Pregabalin as reported in e.g. Synlett 2006, 10, 1589 or with aqueous KOH solution as given in Tetrahedron Letters 2007, 48, 4305.

Preparation of (S)-compound (IVb) form 3-cyano-gluratic acid diethyl ester (VIc)

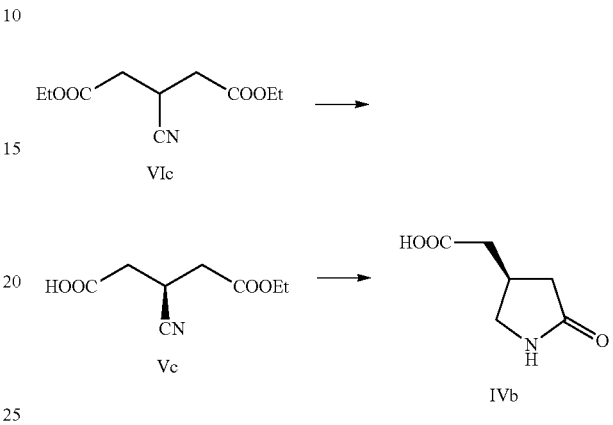

Example 1

The preparation of the starting (S)-compound of formula (IVb) is described in Tetrahedron Asymmetry 2004, 15, 3323.

To a solution of (4R)-4-carboxymethyl-pyrrolidin-2-one (IVb, 14.5 g) in THF (100 ml), cooled to −78° C. under good stirring in inert atmosphere 12% solution of MeMgBr in THF (ca. 1M, 450 ml) was slowly added that the temperature stayed below −50° C. After complete addition the reaction slurry was stirred at −50° C. for 1.5 hrs, then slowly warmed up to rt, stirred for 3 hrs, cooled again to 0° C. and, after slow addition of methyl chloroformate (15 g), stirred at 0° C. for 1 hr and finally poured on aqueous saturated NaHCO$_3$ solution (400 ml). The aqueous phase was extracted 4 times with ethyl acetate (4×100 ml), dried over sodium sulfate, filtered, the filtrate evaporated under reduced pressure to give 19.5 g (90% isolated yield) semi crystalline oily material which was used directly in the next step: For analytical purposes small sample was purified by column chromatography on silica gel (eluens: hexane/Ethyl acetate=10:1): Anal. calculated for C$_{10}$H$_{17}$NO$_4$: C, 55.8; H, 7.96; O N, 6.51; O, 29.73. Found: C, 55.75; H, 8.05; N, 6.40; O, 29.70.

For reduction step, the pyrrolidinone (IIIb, 19.5 g) was dissolved in acetic acid (150 ml) and after addition of 10% Pd—C (1 g) and trifluoroacetic acid (1 ml), the reaction mixture was under vigorous stirring hydrogenated under normal pressure until starting material disappeared. The slurry was filtered to remove the catalyst, the filtrate evaporated under reduced pressure to give 10.2 g (83% isolated yield) (S)-4-isobutyl-pyrrolidin-2-one (IIb) with identical analytical data as reported in Helv. Chim. Acta 1999, 82, 2365 on page 2375 or in Tetrahedron Letters 2007, 48, 4305 or in Org. Proc. Res. & Develop. 1997, 1, 26.

Example 2

To a suspension of diethyl ester (VIc) (23 g) in sodium phosphate buffer solution pH 7.5 (400 ml), PLPA (5 g) was added and the slurry vigorously stirred at rt and pH kept at 7.5 by continuous automatic addition of 2N aqueous NaOH solution. After one equiv. of NaOH has been consumed, the mixture was extracted once with TBME (100 ml), then acidified with 2M HCl to pH 2, after addition of saturated sodium chloride solution (200 ml), the aqueous phase extracted 3 times with methylenechloride (3×200 ml), the combined organic phases dried with sodium sulfate, filtered and the filtrate concentrated under reduced pressure to give (S)-compound (Vc) as slightly yellow oil: 16 g (90% yield) with a 99% ee.

To the crude (S)-acid (Vc) (16 g), dissolved in ethanol (200 ml) Ra—Ni (3 g) was added and the slurry under good stirring at atmospheric pressure hydrogenated until disappearing of the starting material. After filtration of the catalyst and addition of toluene (200 ml) to the filtrate, the solution was heated under reflux to obtain a complete cyclization. The solvents have been then removed under vacuum, the residue dissolved in 5% aqueous NaHCO$_3$ solution, the solution extracted twice with TBME (2×100 ml), the aqueous phase acidified with conc. HCl to pH 3 and the solution evaporated under reduced pressure to dryness. The residue was trituated with methanol (75 ml) to provide a semi crystalline lactam (IVb): 13.9 g (97% yield)

A small sample of (IVb) was purified by column chromatography on silica gel, eluens: hexane/toluene (10:1): Anal. calculated for C$_6$H$_9$NO$_3$: C, 50.53; H, 6.34; N, 9.79; O, 33.53. Found: C, 50.50; H, 6.40; N, 9.70; O, 33.45. Analytical data were identical as reported in Tetrahedron Asymmetry 2004, 15, 3323.

The invention claimed is:

1. A compound of general formula III, having the (S)-configuration as given in formula,

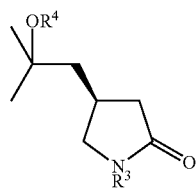

III wherein $R^3$ represents hydrogen and
$R^4$ represents counter cation as alkali or earth alkali metal cation, or hydrogen, or O-protective group, which together with O forms an ester or carbonate, or —$SO_2Cl$ or alkyl- or arylsulfonyl, or thiocarbonyl derivative such as —C(S)Oalkyl or —C(S)Oaryl or —C(S)imidazolyl, and a salt thereof,
in either enantiomerically enriched or enantiomerically pure form.

2. A process for preparation of a compound of general formula III, having the (S)-configuration as given in formula,

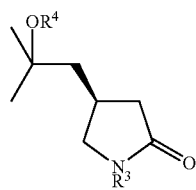

III wherein
$R^3$ represents hydrogen and
$R^4$ represents counter cation as alkali or earth alkali metal cation, or hydrogen, or O-protective group, which together with O forms an ester or carbonate, or alkyl- or arylsulfonyl, or thiocarbonyl derivative such as —C(S)Oalkyl or —C(S)Oaryl or —C(S)imidazolyl, comprising following steps:
a) reaction of the compound of formula IV,

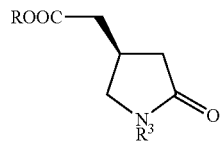

IV wherein R represents hydrogen, linear or brunched $C_{1-6}$-alkyl, aryl, arylalkyl, alkylaryl, and
$R^3$ is the same as defined for compound of formula III;
with a reagent containing $CH_3$-organometallic reagent such as Me-alkali metal or Me-earth alkali metal halide,
b) followed by activation of tert.-hydroxy group according to the definition for $R^4$.

3. A process according to claim 2, wherein the compound of formula III, was subjected reductive removal of —$OR^4$ by reductive displacement of —$OR^4$ group with hydrogen, by homogeneous or heterogeneous hydrogenation in the presence of transition metal such as Ra—Ni, Pt, Pd, Ru or Rh, or with other chemical reducing agent such as metal hydride via $S_{n2}$ displacement of —$OR^4$ group with a hydride, or by a radical-based de-oxygenation in the presence of Triflic or trifluoroacetic acid or Lewis acid, or $Bu_3SnH$ in the presence of $NaBH_4$, or dialkyl phosphites or hypophosphorous acid.

4. A process according to claim 2, wherein the compound of formula IV is reacted with MeLi or MeMgCl and the tert.-alcoholate is treated with methyl chloroformate or Mesylchloride and the —$OR^4$ group then reductively removed with hydrogen in the presence of transition metal catalyst such as Ra—Ni, Pt, Pd or Rh.

5. A process according to claim 2, wherein the compound of formula IV is reacted with MeMgCl and the tert.-alcoholate treated with methyl chloroformate or Mesylchloride, and —$OR^4$ group reductively removed with $Et_3SiH$, $Cl_3SiH$, tris(trimethylsilyl)-silane, tetramethyldisiloxane in the presence of Triflic or trifluoroacetic acid or $AlCl_3$ or $TiCl_4$.

\* \* \* \* \*